US008652454B2

(12) United States Patent
Murray et al.

(10) Patent No.: US 8,652,454 B2
(45) Date of Patent: Feb. 18, 2014

(54) COMPOSITION

(75) Inventors: Andrew Malcolm Murray, Wirral (GB); Claire Louise Richards, Wirral (GB)

(73) Assignee: Conopco Inc., Englewood Cliffs, NJ (US)

( * ) Notice: Subject to any disclaimer, the term of this patent is extended or adjusted under 35 U.S.C. 154(b) by 52 days.

(21) Appl. No.: 13/266,242

(22) PCT Filed: Apr. 27, 2010

(86) PCT No.: PCT/EP2010/055590
§ 371 (c)(1),
(2), (4) Date: Dec. 6, 2011

(87) PCT Pub. No.: WO2010/136285
PCT Pub. Date: Dec. 2, 2010

(65) Prior Publication Data
US 2012/0093757 A1   Apr. 19, 2012

(30) Foreign Application Priority Data
May 28, 2009  (EP) .................................... 09161386

(51) Int. Cl.
*A61K 8/72*   (2006.01)
(52) U.S. Cl.
USPC ...................... 424/70.12; 424/70.27; 514/880
(58) Field of Classification Search
None
See application file for complete search history.

(56) References Cited

U.S. PATENT DOCUMENTS

| 4,886,660 A | 12/1989 | Patel |
| 5,714,136 A | 2/1998 | Yahagi |
| 6,849,252 B1 * | 2/2005 | Yang et al. ................. 424/70.11 |
| 2003/0003073 A1 | 1/2003 | Muller |

FOREIGN PATENT DOCUMENTS

| EP | 0407040 | 1/1991 |
| EP | 0530974 | 3/1993 |
| EP | 1258236 | 11/2002 |
| WO | WO9631188 | 10/1996 |
| WO | WO9714396 | 4/1997 |
| WO | WO0117502 | 3/2001 |
| WO | WO0185108 | 11/2001 |
| WO | WO2005025525 | 3/2005 |
| WO | WO2005039517 A1 | 5/2005 |

OTHER PUBLICATIONS

PCT International Search Report in PCT application PCT/EP2010/055590 dated Jul. 26, 2010 with Written Opinion.
EP Search Report in EP application EP 09 16 1386 dated Oct. 8, 2009.

* cited by examiner

*Primary Examiner* — Lezah Roberts
*Assistant Examiner* — Nannette Holloman
(74) *Attorney, Agent, or Firm* — Ronald A. Koatz

(57) ABSTRACT

Hair conditioner comprising silicone and a conditioning gel phase, said phase obtainable by heating a fatty alcohol and an oil until they are molten, separately heating a cationic surfactant in water until it is dissolved/suspended, then adding the molten fatty alcohol and oil mix to the cationic surfactant before adding any remaining ingredients.

3 Claims, No Drawings

COMPOSITION

The present invention relates to an improved conditioning composition.

Despite the prior art there remains a need for improved conditioning compositions.

Accordingly, there is provided a hair conditioner comprising silicone and a conditioning gel phase, said phase obtainable by heating a fatty alcohol and an oil until they are molten, separately heating a cationic surfactant in water until it is dissolved/suspended, then adding the molten fatty alcohol and oil mix to the cationic surfactant before adding any remaining ingredients.

Surprisingly, the conditioner according to the invention is capable of delivering silicone to the hair surface and thereby produce a desirable conditioning benefit.

Preferably, the oil is a light mineral oil. Preferably, the light mineral oil has a density of from 0.7 to 0.85 g/ml.

Preferably, the composition as a whole comprises less than 2% wt. anionic surfactant.

Preferably, the composition as a whole comprises substantially no anionic surfactant.

Such a conditioning gel phase is common in the art and means an arrangement of cationic surfactant and fatty materials which are capable of conditioning hair. Silicones are also be present in the formulation but are typically not part of the conditioning gel phase.

The conditioning surfactants are cosmetically acceptable and suitable for topical application to the hair.

Suitable conditioning surfactants are selected from cationic surfactants, used singly or in admixture. Examples include quaternary ammonium hydroxides or salts thereof, e.g. chlorides.

Suitable cationic surfactants for use in hair conditioners of the invention include cetyltrimethylammonium chloride, behenyltrimethylammonium chloride, cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, cocotrimethylammonium chloride, and the corresponding hydroxides thereof. Further suitable cationic surfactants include those materials having the CTFA designations Quaternium-5, Quaternium-31 and Quaternium-18. Mixtures of any of the foregoing materials may also be suitable. A particularly useful cationic surfactant for use in hair conditioners of the invention is cetyltrimethylammonium chloride, available commercially, for example as DEHYQUART, ex Henkel.

In conditioners of the invention, the level of cationic surfactant is preferably from 0.01 to 10%, more preferably 0.05 to 5%, most preferably 0.1 to 2% by weight of the composition.

The conditioning gel phase of the invention advantageously incorporates a fatty alcohol material. The combined use of fatty alcohol materials and cationic surfactants in conditioning compositions is believed to be especially advantageous, because this leads to the formation of a lamellar phase, in which the cationic surfactant is dispersed.

Representative fatty alcohols comprise from 8 to 22 carbon atoms, more preferably 16 to 20. Examples of suitable fatty alcohols include cetyl alcohol, stearyl alcohol and mixtures thereof. The use of these materials is also advantageous in that they contribute to the overall conditioning properties of compositions of the invention.

The level of fatty alcohol material in conditioners of the invention is conveniently from 0.01 to 10%, preferably from 0.1 to 5% by weight of the composition. The weight ratio of cationic surfactant to fatty alcohol is suitably from 10:1 to 1:10, preferably from 4:1 to 1:8, optimally from 1:1 to 1:4.

The resulting formulation comprising a conditioning gel phase also comprises a silicone.

The silicone is insoluble in the aqueous matrix of the composition and so is present in an emulsified form, with the silicone present as dispersed particles.

Suitable silicones include polydiorganosiloxanes, in particular polydimethylsiloxanes which have the CTFA designation dimethicone. Also suitable for use compositions of the invention (particularly shampoos and conditioners) are polydimethyl siloxanes having hydroxyl end groups, which have the CTFA designation dimethiconol. Also suitable for use in compositions of the invention are silicone gums having a slight degree of cross-linking, as are described for example in WO 96/31188. These materials can impart body, volume and stylability to hair, as well as good wet and dry conditioning.

The viscosity of the emulsified silicone itself (not the emulsion or the final hair conditioning composition) is typically at least 10,000 cst. In general we have found that conditioning performance increases with increased viscosity. Accordingly, the viscosity of the silicone itself is preferably at least 60,000 cst, most preferably at least 500,000 cst, ideally at least 1,000,000 cst. Preferably the viscosity does not exceed $10^9$ cst for ease of formulation.

Emulsified silicones for use in hair shampoos and conditioners of the invention will typically have an average silicone particle size in the composition of less than 30, preferably less than 20, more preferably less than 10 microns. We have found that reducing the particle size generally improves conditioning performance. Most preferably the average silicone particle size of the emulsified silicone in the composition is less than 2 microns, ideally it ranges from 0.01 to 1 micron. Silicone emulsions having an average silicone particle size of ≤0.15 microns are generally termed microemulsions.

Particle size may be measured by means of a laser light scattering technique, using a 2600D Particle Sizer from Malvern Instruments.

Suitable silicone emulsions for use in the invention are also commercially available in a pre-emulsified form.

Examples of suitable pre-formed emulsions include emulsions DC2-1766, DC2-1784, and microemulsions DC2-1865 and DC2-1870, all available from Dow Corning. These are all emulsions/microemulsions of dimethiconol. Cross-linked silicone gums are also available in a pre-emulsified form, which is advantageous for ease of formulation. A preferred example is the material available from Dow Corning as DC X2-1787, which is an emulsion of cross-linked dimethiconol gum. A further preferred example is the material available from Dow Corning as DC X2-1391, which is a microemulsion of cross-linked dimethiconol gum.

A further preferred class of silicones for inclusion in shampoos and conditioners of the invention are amino functional silicones. By "amino functional silicone" is meant a silicone containing at least one primary, secondary or tertiary amine group, or a quaternary ammonium group.

Examples of suitable amino functional silicones include:
(i) polysiloxanes having the CTFA designation "amodimethicone", and the general formula:

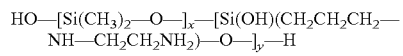

in which x and y are numbers depending on the molecular weight of the polymer, generally such that the molecular weight is between about 5,000 and 500,000.

(ii) polysiloxanes having the general formula:

in which:

G is selected from H, phenyl, OH or $C_{1-8}$ alkyl, e.g. methyl;

a is 0 or an integer from 1 to 3, preferably 0;

b is 0 or 1, preferably 1;

m and n are numbers such that (m+n) can range from 1 to 2000, preferably from 50 to 150;

m is a number from 1 to 2000, preferably from 1 to 10;

n is a number from 0 to 1999, preferably from 49 to 149, and

R' is a monovalent radical of formula —$C_qH_{2q}$L in which q is a number from 2 to 8 and L is an aminofunctional group selected from the following:

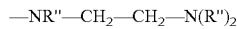

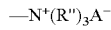

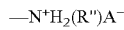

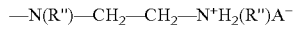

in which R" is selected from H, phenyl, benzyl, or a saturated monovalent hydrocarbon radical, e.g. $C_{1-20}$ alkyl, and;

A is a halide ion, e.g. chloride or bromide.

Suitable amino functional silicones corresponding to the above formula include those polysiloxanes termed "trimethylsilylamodimethicone" as depicted below, and which are sufficiently water insoluble so as to be useful in compositions of the invention:

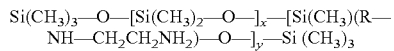

wherein x+y is a number from about 50 to about 500, and wherein R is an alkylene group having from 2 to 5 carbon atoms. Preferably, the number x+y is in the range of from about 100 to about 300.

(iii) quaternary silicone polymers having the general formula:

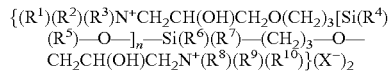

wherein $R^1$ and $R^{10}$ may be the same or different and may be independently selected from H, saturated or unsaturated long or short chain alk(en)yl, branched chain alk(en)yl and $C_5$-$C_8$ cyclic ring systems;

$R^2$ thru' $R^9$ may be the same or different and may be independently selected from H, straight or branched chain lower alk(en)yl, and $C_5$-$C_8$ cyclic ring systems;

n is a number within the range of about 60 to about 120, preferably about 80, and $X^-$ is preferably acetate, but may instead be for example halide, organic carboxylate, organic sulphonate or the like.

Suitable quaternary silicone polymers of this class are described in EP-A-0 530 974.

Amino functional silicones suitable for use in shampoos and conditioners of the invention will typically have a mole % amine functionality in the range of from about 0.1 to about 8.0 mole %, preferably from about 0.1 to about 5.0 mole %, most preferably from about 0.1 to about 2.0 mole %. In general the amine concentration should not exceed about 8.0 mole % since we have found that too high an amine concentration can be detrimental to total silicone deposition and therefore conditioning performance.

The viscosity of the amino functional silicone is not particularly critical and can suitably range from about 100 to about 500,000 cst.

Specific examples of amino functional silicones suitable for use in the invention are the aminosilicone oils DC2-8220, DC2-8166, DC2-8466, and DC2-8950-114 (all ex Dow Corning), and GE 1149-75, (ex General Electric Silicones).

Also suitable are emulsions of amino functional silicone oils with non ionic and/or cationic surfactant.

Suitably such pre-formed emulsions will have an average amino functional silicone particle size in the shampoo composition of less than 30, preferably less than 20, more preferably less than 10 microns. Again, we have found that reducing the particle size generally improves conditioning performance. Most preferably the average amino functional silicone particle size in the composition is less than 2 microns, ideally it ranges from 0.01 to 1 micron. Silicone emulsions having an average silicone particle size of ≤0.15 microns are generally termed microemulsions.

Pre-formed emulsions of amino functional silicone are also available from suppliers of silicone oils such as Dow Corning and General Electric. Specific examples include DC929 Cationic Emulsion, DC939 Cationic Emulsion, and the non-ionic emulsions DC2-7224, DC2-8467, DC2-8177 and DC2-8154 (all ex Dow Corning).

An example of a quaternary silicone polymer useful in the present invention is the material K3474, ex Goldschmidt.

The total amount of silicone incorporated into compositions of the invention depends on the level of conditioning desired and the material used. A preferred amount is from 0.01 to about 10% by weight of the total composition although these limits are not absolute. The lower limit is determined by the minimum level to achieve conditioning and the upper limit by the maximum level to avoid making the hair and/or skin unacceptably greasy.

We have found that a total amount of silicone of from 0.3 to 5%, preferably 0.5 to 3%, by weight of the total composition is a suitable level.

Density of the mineral oil is also known as specific gravity and is measured according to ASTM D 4052 at 15.6 C.

EXAMPLE 1

A composition according to an embodiment of the invention.

| % w/w | Trade Name |
|---|---|
| 1.25 | Stearamidopropyl dimethylamine |
| 86.59 | WATER, CHLORINATED DEMINERALISED |
| 1 | Mineral oil |
| 0.1 | DISODIUM EDTA |
| 1.25 | Behenyl trimethyl ammonium chloride |
| 5 | Cetearyl alcohol |
| 0.1 | SODIUM CHLORIDE |
| 0.06 | CIT/MIT |
| 0.5 | Parfum |
| 0.2 | Methyl Paraben |
| 0.38 | Lactic Acid |
| 3.57 | DC 5-7134 9:1 600K/8566 CTAC 70% |

EXAMPLE 2

A process for making a composition according to the invention.

1. Add mineral oil to side pot and heat to 50° C. Add cetearyl alcohol and melt out keeping T at 75° C.
2. Add water to mixer and start heating to 85° C.
3. Mix with Silverson.
4. Add methyl paraben and disperse then lactic acid and disperse.
5. At 60 C add stearamidopropyl dimethylamone over top and disperse. At 80° C. add behenyl trimethyl ammonium chloride and disperse.
6. At 85° C. with mixing inject molten cetearyl alcohol and mineral oil mixture into loop. Mix for 30 mins.
7. Start jacket cooling to 30° C. without mixing.
8. Add quench water then other ingredients such as perfumes, etc.

EXAMPLE 3

Evidence illustrating how the composition of the invention delivers more silicone than a comparative composition comprising heavy mineral oil.

|  | A | B | C |
|---|---|---|---|
| Silicone deposition (ppm) | 2157.89 | 2197.47 | 1294.59 |

A: Control, no oil
B: Test sample, light mineral oil
C: Comparative, heavy mineral oil Table shows that compositions according to the invention deliver more silicone than compositions comprising heavy mineral oil.

The invention claimed is:

1. Hair conditioner comprising silicone and a conditioning gel phase, said phase obtainable by heating a fatty alcohol and a light mineral oil having a density of from 0.7 to 0.85 g/ml. until they are molten, separately heating a cationic surfactant in water until it is dissolved/suspended, then adding the molten fatty alcohol and oil mix to the cationic surfactant before adding any remaining ingredients; wherein compositions comprising light mineral oil having said defined density deliver more silicone than compositions comprising heavy mineral oil having higher density.

2. Composition according to claim 1 wherein the composition as a whole comprises less than 2% wt. anionic surfactant.

3. Composition according to claim 1 wherein the composition as a whole comprises no anionic surfactant.

* * * * *